(12) United States Patent  (10) Patent No.: US 8,276,464 B2
Krause et al.  (45) Date of Patent: Oct. 2, 2012

(54) TRANSVERSE LOAD APPARATUS

(75) Inventors: Roger A. Krause, Howell, MI (US);
Christopher Hall, New Hudson, MI (US); Sherif Gindy, Macomb, MI (US)

(73) Assignee: Mahle International GmbH (DE)

( * ) Notice: Subject to any disclaimer, the term of this patent is extended or adjusted under 35 U.S.C. 154(b) by 249 days.

(21) Appl. No.: 12/685,217

(22) Filed: Jan. 11, 2010

(65) Prior Publication Data
US 2011/0167922 A1 Jul. 14, 2011

(51) Int. Cl.
*G01N 3/02* (2006.01)
(52) U.S. Cl. ............................................. 73/856; 73/808
(58) Field of Classification Search .................. 73/760, 73/796, 808, 856–860
See application file for complete search history.

(56) References Cited

U.S. PATENT DOCUMENTS

| | | | | |
|---|---|---|---|---|
| 4,478,086 A | * | 10/1984 | Gram | 73/781 |
| 4,748,854 A | * | 6/1988 | Rao | 73/799 |
| 5,425,276 A | * | 6/1995 | Gram et al. | 73/816 |
| 6,718,833 B2 | * | 4/2004 | Xie et al. | 73/812 |
| 6,732,591 B2 | * | 5/2004 | Miles et al. | 73/808 |
| 6,813,960 B1 | * | 11/2004 | Owen et al. | 73/808 |

FOREIGN PATENT DOCUMENTS

| | | |
|---|---|---|
| GB | 2324876 A | 11/1998 |
| JP | 2000097833 A | 4/2000 |
| JP | 2007178351 A | 7/2007 |

OTHER PUBLICATIONS

International Search Report for PCT/EP2010/007945, Apr. 2011.
English abstract for JP-2007178351, Jul. 2007.
English abstract for JP-2000097833, Apr. 2000.

* cited by examiner

*Primary Examiner* — Max Noori
(74) *Attorney, Agent, or Firm* — Rader, Fishman & Grauer PLLC

(57) ABSTRACT

A loading device is provided, including a first member, a second member, a first clamping member, a second clamping member, and an actuator. The first member includes a first surface, where the first surface contacts a first side of a test piece. The second member includes a second surface, for contacting a second side of the test piece. The first clamping member includes a first clamping surface for contacting the second side of the test piece. The second clamping member is fixedly secured to the second member. The actuator exerts a predetermined force driving the second member in a first direction away from the first member, and a second direction towards the first member.

23 Claims, 5 Drawing Sheets

TRANSVERSE LOAD APPARATUS

TECHNICAL FIELD

The present disclosure relates to a loading device, and in particular to a loading device exerting a predetermined force on a test piece.

BACKGROUND

The traditional internal combustion engine relies on connecting rods for transmitting combustion power from a piston main body to a crankshaft of the engine, thereby converting the linear motion of the piston main body to rotational motion at the crankshaft. The connecting rod includes a crankshaft or big end surrounding the crankshaft, and a piston pin or small end that receives a piston or wrist pin. For ease of assembly to the crankshaft, the crankshaft end of the connecting rod may be sectioned into two portions. The first portion is part of the main body of the connecting rod, while the second portion is a separate cap that is secured to the first portion. The first portion may be secured to the cap by fasteners extending through bores in the cap to engage threaded bores in the first portion.

During operation of the engine, the fasteners securing the cap to the crankshaft end of the connecting rod sometimes become loose or separate from the bores. In particular, fastener separation depends on factors such as fastener pre-load, thread geometry and coating. Other factors may also include engine parameters such as revolutions per minute (RPM), resonance frequency, and transverse loads exerted on the connecting rod caused by crankpin and/or crank throw bending and crankpin to cylinder misalignment. Therefore, the connecting rod typically undergoes testing where the connecting rod is operated within an engine, e.g., simulating adverse operating conditions, in an effort to ensure that the fasteners remain secured within the bores during the normal operating life of the engine. During testing, the engine may be operated for at least several hundred hours to ensure that the fasteners remain secured to the first portion of the crankshaft end of the connecting rod. However, operating an engine for extended periods of time to perform this type of testing may become time-consuming and costly, as operating an engine for an extended period of time typically requires a substantial amount of fuel to power the engine. The complexity of engine assemblies may also lead to difficulties in repeating test results, as test engines may not accurately re-create identical operating conditions for the connecting rods. Moreover, many engine components or even the entire engine might need to be replaced after testing. Additionally, contaminants may be generated that could be minimized using a different mechanism.

Therefore, there exists a need to provide a device that simulates the loading conditions that may occur at the crankshaft end of a connecting rod during operation of a reciprocating engine.

DETAILED DESCRIPTION

Figure 1:
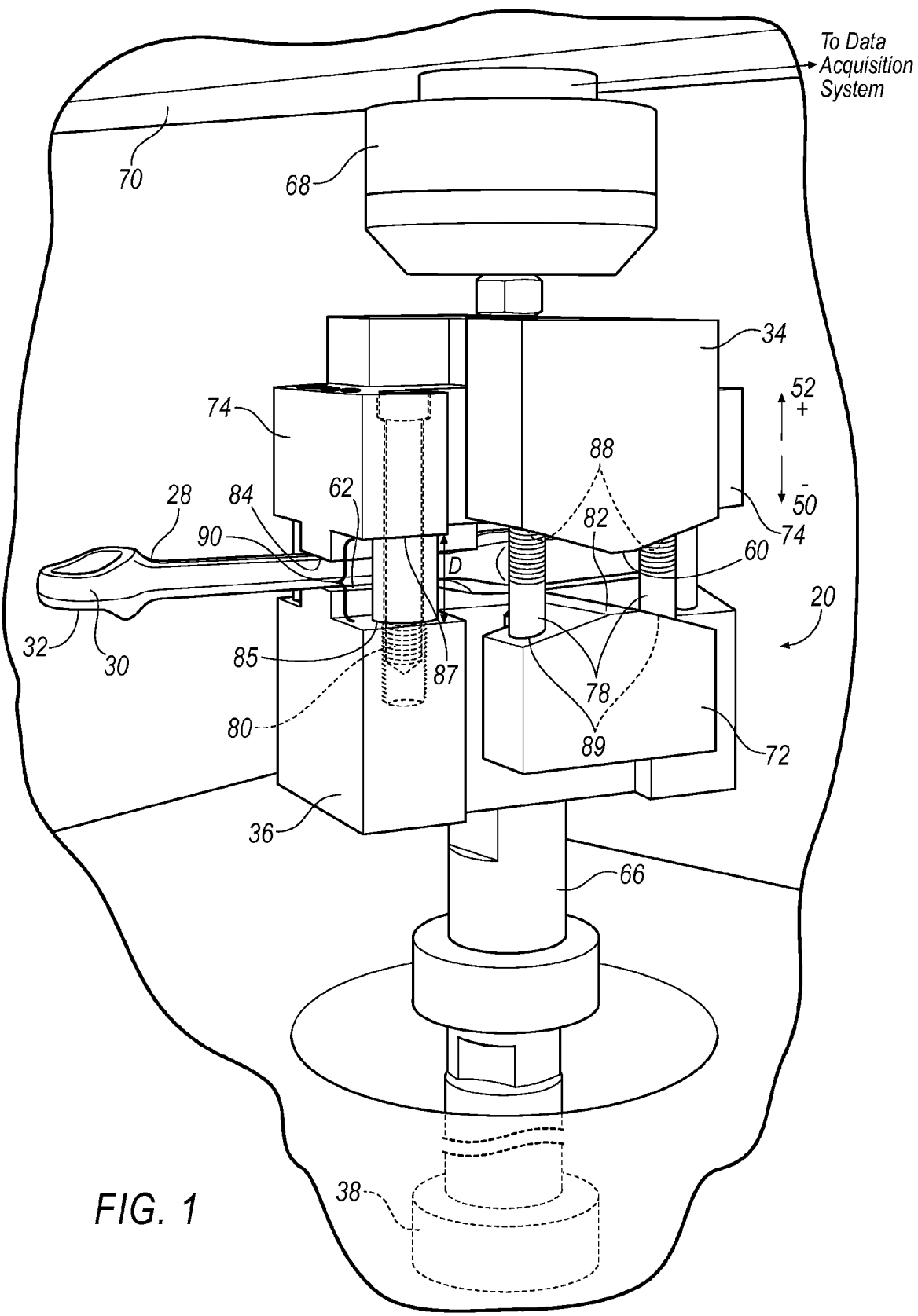
FIG. 1 is a perspective view of a loading assembly including a test piece.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Moreover, a number of constants may be introduced in the discussion that follows. In some cases illustrative values of the constants are provided. In other cases, no specific values are given. The values of the constants will depend on characteristics of the associated hardware and the interrelationship of such characteristics with one another as well as environmental conditions and the operational conditions associated with the disclosed system.

Figure 2:
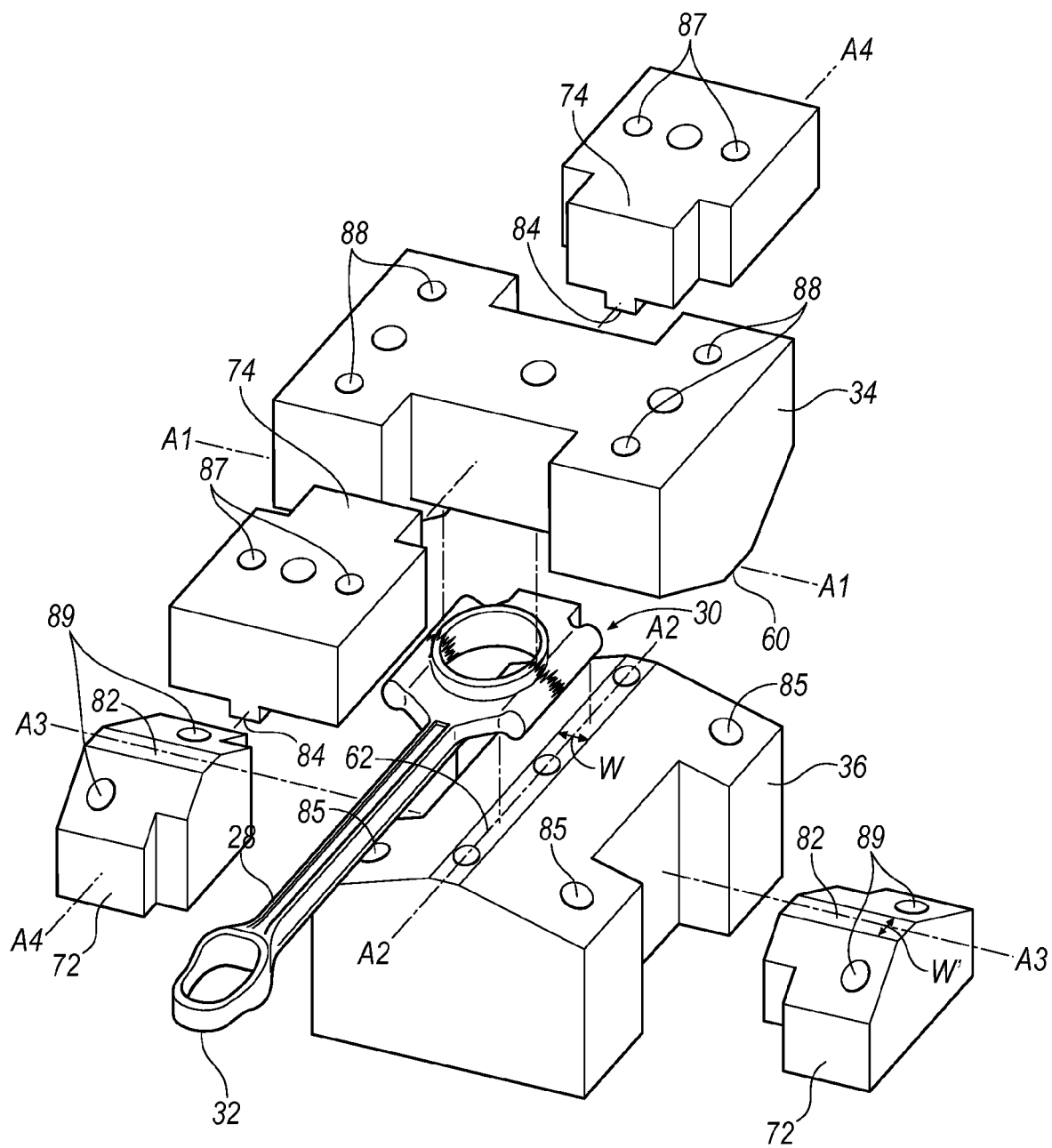
FIG. 2 is a partially exploded view of the loading assembly and the test piece, the loading assembly including a first member, a second member, a first clamping member and a second clamping member.

FIG. 1 illustrates an exemplary loading device 20 clamping a test piece 30. The test piece 30 is illustrated as a connecting rod and includes a first side 28 and a second side 32, where the first side 28 generally opposes the second side 32. The loading device 20 includes a first member 34, a second member 36, and an actuator 38 in mechanical communication with the second member 36. The first and second members 34 and 36 may be fixtures clamping the test piece 30 in place within the loading device 20. Referring generally to FIGS. 1 and 2, the loading device 20 also includes two pairs of clamps, a pair of first clamping members or clamps 72 and a pair of second clamping members or clamps 74. The first pair of clamps 72 may be connected to the first member 34 by first fasteners 78, and the second pair of clamps 74 may be fixedly secured to the second member 36 by second fasteners 80. Additionally, spacers 90 are provided that define a predetermined spacing between the clamps 74 and second member 36. Accordingly, the first and second fasteners 78, 80 and spacers 90 may generally allow adjustment of a relative position of the clamps 72, 74 and the members 34, 36, respectively, e.g., to accommodate test pieces or connecting rods of different sizes.

Referring to FIG. 1, the first member 34 is generally fixed to a frame having a stationary beam 70 via a load cell 68. The actuator 38 drives the second member 36 in a first direction 50 that is oriented away from the first member 34, and a second direction 52 that is oriented towards the first member 34. In particular, the actuator 38 may be in mechanical communication with the second member 36, where the actuator 38 exerts a predetermined force on the second member 36 as the second member 36 is driven in the first and second directions 50 and 52. Turning to FIG. 2, which is an exploded view of the loading device 20, the first member 34 includes a first surface 60 that contacts the first side 28 of the test piece 30 in the assembled loading device 20. As best seen in FIG. 2, the first surface 60 may be elongated, defining a first longitudinal axis A1-A1 that is longitudinal with respect to the first surface 60.

The second member 36 includes a second surface 62 that may also be elongated such that it defines a second longitudinal axis A2-A2 extending longitudinally with respect to the second surface 62. The second surface 62 may be positioned generally perpendicular to the first surface 60, and contacts the second side 32 of the test piece 30 in the assembled loading device 20. That is, the first surface 60 may be positioned such that the first longitudinal axis A1-A1 is generally perpendicular to the second longitudinal axis A2-A2 of the second surface 62. The first and second surfaces 60, 62 may thus be configured to apply respective edge loads to the test piece 30 that are generally orthogonal to each other, as will be explained further below. The first pair of clamps 72 includes a first clamp surface 82, and the second pair of clamps 74 includes a second clamp surface 84. The first pair of clamps 72 may cooperate to define a longitudinal axis A3-A3, while the second pair of clamps cooperate to define a longitudinal axis A4-A4, where each of the axes A3-A3, A4-A4 are generally perpendicular to each other. When assembled to the loading device 20, the first clamp surface 82 contacts the second side 32 of the test piece 30 and the second clamp surfaces 84 contact the first side 28 of the test piece 30.

Referring to FIG. 1, the second clamp surface 84 may be generally aligned with the second surface 62 of the second member 36, and the second member 36 may be fixedly secured to the second pair of clamps 74 when the loading device 20 is assembled. Accordingly, the axes A2-A2, A4-A4 may be generally aligned parallel to each other. The first clamping surface 82 contacts the second side 32 of the test piece 30 and may be positioned generally perpendicular to the second clamping surface 84. When the second member 36 is driven away from the first member 34, i.e., in the first direction 50 shown in FIG. 1, the second pair of clamps 74 exert the predetermined force on the test piece 30. When the second member 36 is driven in the second direction 52 toward the first member, the second member 36 exerts the predetermined force on the test piece 30. The second pair of clamps 74 and the second member 36 exert the predetermined force on the test piece 30 to create bending moments in the test piece 30. These bending moments may thus be predetermined, as will be described further below. The predetermined force may be communicated from the actuator 38 to the second member 36 at a predetermined frequency rate.

In one illustration of the loading device 20, the predetermined frequency may be adjustable in value and correlate generally with a rotational speed, e.g., RPM, of an associated reciprocating engine. More specifically, the predetermined frequency substantially simulates about the same frequency that a connecting rod would experience while operating in an exemplary reciprocating engine at a specific RPM. The predetermined frequency value can be adjusted to represent different RPM values. The reciprocating engine may be selected from any type of engine including one or more reciprocating pistons, such as, for example, an internal combustion engine.

The predetermined force and resulting bending moment may also be adjustable in value and correlate generally with a transverse load exerted on a connecting rod of a reciprocating engine. More specifically, the predetermined force substantially simulates the load that a crankshaft end of a connecting rod may experience while operating in a reciprocating engine. The transverse load is typically caused by crankpin bending and crankpin to cylinder misalignment that occurs in some reciprocating engines. This is because reciprocating engines usually have some degree of bending in the crankpin and/or crank throw as well as some degree of crank throw to cylinder misalignment.

The transverse load may be defined as a load exerted on a crankshaft end of a connecting rod that is generally perpendicular to an axis of a corresponding cylinder in operation with the connecting rod. The transverse load may also be generally parallel with respect to a longitudinal axis of a crankshaft in communication with the crankshaft end of the connecting rod. The predetermined force exerted by the actuator 38 and onto the test piece 30 corresponds to the transverse load exerted on the crankshaft end of the connecting rod. Therefore, the test piece 30 may be placed on the loading device 20 with the predetermined force exerted on the test piece 30 at the predetermined frequency in an effort to simulate about the same loads exerted on a crankshaft end of a connecting rod operated within a reciprocating engine at specified operating conditions. The predetermined force may be adjusted independently of the predetermined frequency value, however, the predetermined force may also be adjusted in relation to the predetermined frequency value as well.

In one exemplary illustration of the loading device 20, the predetermined force is between about 2 kN and about 30 kN, and the predetermined frequency value is between about 10 Hz and about 100 Hz. The predetermined loading frequency represents the engine reciprocating speed in rotations per minute (RPM) divided by 120, where the engine RPM is first divided by the value 60 to convert the RPM value into cycles per second (Hertz). Then the value is divided by the value 2, because there is one power cycle for every two crank revolutions in a four stroke engine. For two-stroke engine applications the final step of dividing by 2 is not necessary as there is a power cycle in each revolution of the engine. As one specific example, in one illustration the engine speed may be about 4000 RPM, which corresponds to about 33 Hz.

Continuing to refer to FIG. 1, the loading device 20 is illustrated in the clamped position, where the first and second surfaces 60 and 62 contact the first and second sides 28 and 32 of the test piece 30, respectively. It should be noted that while FIG. 1 illustrates the first member 34 positioned above the second member 36, the loading device 20 may also be arranged in the opposite direction, i.e., with the second member 36 positioned above the first member 34, laterally, or any other arrangement that is convenient.

Turning to FIG. 2, the first and second surfaces 60 and 62 may be generally longitudinally oriented surfaces with a generally narrow width W, where the width W of the surfaces 60 and 62 are sized to create an edge load on the test piece 30. In one exemplary illustration, the first and second surfaces 60 and 62 may include a width W of about between 2 mm and 3 mm. The first clamp surface 82 and the second clamp surface 84 are also similar, with generally longitudinally oriented surfaces with a width W' sized for creating an edge load as well. In one exemplary illustration, the first and second clamp surfaces 82 and 84 may also include a width of about between 2 mm and 3 mm.

FIG. 1 illustrates the first member 34 positioned generally perpendicular to the second member 36. The actuator 38 may be any type of actuator that exerts a predetermined force at a specified frequency, such as, for example, a pneumatically or hydraulically powered actuator. FIG. 1 also illustrates the actuator 38 in communication with the second member 36 by a shaft 66, however the actuator 38 may also be in communication with the second member 36 through a series of linkages as well. Alternatively, the actuator 38 may also be in direct communication with the second member 36 as well, and the shaft 66 may be omitted.

The first member 34 may be in a generally fixed position adjacent a load cell 68, with the load cell 68 positioned against a stationary beam 70. The load cell 68 measures tension and compression forces that are exerted by the actuator 38 to the first and second members 34 and 36. The load cell 68 may be in electrical communication with a data acquisition system (not shown), where the load cell 68 communicates the tension and compression force data to the data acquisition system. The stationary beam 70 provides support to and allows for the first member 34 to remain generally stationary even as the actuator 38 exerts the predetermined force in the first direction 50, forcing any deflection caused by the loading of the actuator to be generally confined to the test piece 32.

The first pair of clamps 72 is each assembled to the first member 34, and the second pair of clamps 74 are each assembled to the second member 36. The first pair of clamps 72 may thus be selectively fixed to the first member 34, and the second pairs of clamps 74 may each be selectively fixed to the second member 36. The first clamp surface 82 contacts the second side 32 of the test piece 30, and the second clamp surface 84 contacts the first side 28 of the test piece 30. The first fasteners 78 may be connected to the first member 34 by a threaded engagement, where the first fasteners 78 engage within first apertures 88 of the first member 34 and with first apertures 89 of the first pair of clamps 72 (FIGS. 1 and 2). The second fasteners 80 may also be fixedly connected to the second member 36 by a threaded engagement, where the second fasteners 80 engage within second apertures 85 of the second member 36 and apertures 87 of the second clamping members 74 (FIGS. 1 and 2).

The second fasteners 80 include spacers 90, where the spacers fixedly connect the second pair of clamps 74 to the second member 36. That is, the spacers fixedly connect the second pair of clamps 74 to the second member 36, such that the second pair of clamps 74 is positioned at a predetermined distance D from the second member 36. The predetermined distance D generally remains constant as the actuator 38 drives the second member in the first direction 50 and the second direction 52. The spacers may also allow for the second pair of clamps 74 to clamp the test piece 30 securely to the second member 36. In contrast, the first fasteners 78 may be threaded bolts that allow the first pair of clamps 72 to be adjusted in relation with the first member 34, e.g., to fit test pieces having a different thicknesses.

Figure 3A:
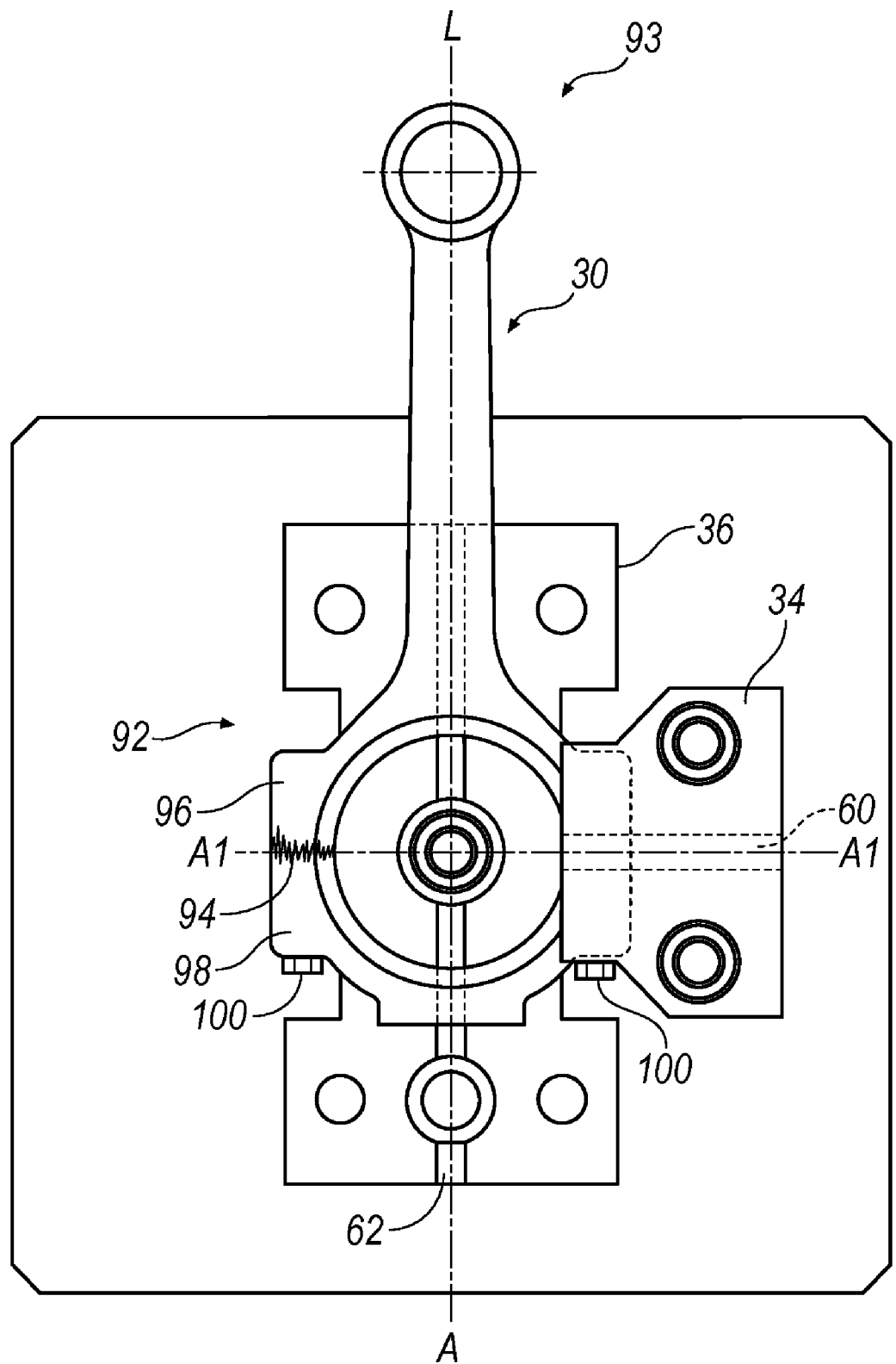
FIG. 3A is a partial cutaway plan view of the test piece clamped between the first member and the second member of the loading device.

FIG. 3A is a partially sectioned view of the test piece 30 loaded between the first member 34 and the second member 36. The test piece 30 is illustrated as a connecting rod, where a crankshaft end 92 of the connecting rod is clamped between the first member 34 and the second member 36 in a predetermined orientation, exemplified here as perpendicular. The crankshaft end 92 of the connecting rod is illustrated as a fracture split type connecting rod, where the connecting rod is split along an axis B-B (shown in FIG. 4) creating a split line 94. The fracture-type split line 94 is typically created when the connecting rod is fractured into two pieces in a manufacturing operation commonly known as cracking. Specifically, the connecting rod may be fractured into a first portion 96 and a second portion or cap 98. The first portion 96 and the cap 98 may be held together at the split line 94 by fasteners 100, which are illustrated as bolts. The connecting rod is illustrated with a piston pin end 93 remaining generally free in the loading device 20, where the piston pin end 93 is generally not tested in the loading device 20. In one example, the piston pin end 93 may even be removed from the connecting rod prior to being placed in the loading device 20.

Although FIG. 3A illustrates the connecting rod with a split line 94 created by cracking, it should be noted that the split line 94 may be created by other manufacturing operations as well, such as, for example, split machining. However, it may be advantageous to include a split line 94 created by cracking, because fractured portions of the connecting rod generally produce a more precise fit when assembled together when compared to machining. In addition, connecting rods with no fracture or split line may also be tested.

The longitudinal axis A2-A2 of the second surface 62 of the second member 36 (best seen in FIG. 2) is illustrated as being generally perpendicular to the split line 94, while the longitudinal axis A1-A1 first surface 60 of the first member 34 (best seen in FIG. 2) is illustrated as being generally parallel to and in contact with the split line 94. As the second member 36 exerts the predetermined force in the second direction 52 towards the first member 34 (illustrated in FIG. 1), the first member 34 remains relatively stationary while the second member 36 and the second surface 62 exerts the predetermined force upon the test piece 30. The relative movement between the first and second members 34 and 36 creates a first bending movement in the crankshaft end 92 of the connecting rod, where there is approximately zero displacement at the split line 94, and about maximum displacement at a longitudinal axis L-A of the connecting rod. That is, the first bending movement of the crankshaft end 92 may be at about a minimum value at the fracture split line 94 of the crankshaft end 92, and about a maximum value at the longitudinal axis L-A of the connecting rod as the second member 36 exerts force on the test piece 30. The first bending movement of the test piece 30 thus imparts a bending moment about a moment axis B-B (shown in FIG. 4) that is aligned generally parallel to an interface between the cap portion 98 and first portion 96 of the test piece 30, e.g., the split line 94.

Figure 3B:
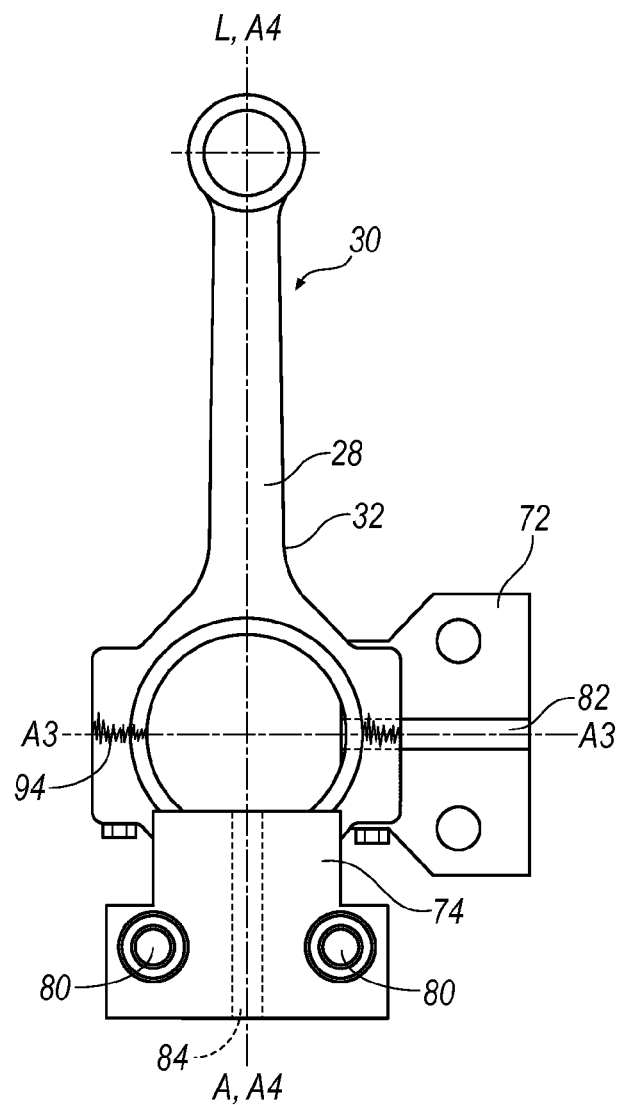
FIG. 3B is a partial cutaway plan view of the test piece clamped between the first clamping member and the second clamping member of the loading device.

FIG. 3B illustrates the test piece 30 loaded between one of the first pair of clamps 72 including first clamp surface 82, and one of the second pair of clamps 74 including the second clamp surface 84. When assembled to the loading device 20 (FIG. 1), the first clamp surface 82 contacts the second side 32 of the test piece 30 and the second clamp surface 84 contacts the first side 28 of the test piece 30. As the second member 36 is driven in the first direction 50 (FIG. 1), the second clamp surfaces 84 exerts the predetermined force on the test piece 30, where the second clamp surfaces 84 may be generally aligned with the second surface 62 located on the opposing side of the test piece 30 (FIG. 3A), and positioned generally perpendicular to the split line 94. As the second member 36 (FIG. 3A) is driven in the first direction 50, the first clamp surfaces 82 are translated with respect to the second clamp surface 84 as a result of relative movement between the first and second pairs of clamps 72, 74.

The relative movement between the first and second pairs of clamps 72 and 74 create the bending moment in the test piece 30 about the fracture split line 94 described above. Further, the relative movement between the first and second pairs of clamps 72, 74 may also create a second bending movement in the crankshaft end 92 of the connecting rod. The second bending movement in the test piece 30 may generally result from the constraint of the test piece 30 along the longitudinal axis L-A between the second surface 62 and second clamp surfaces 84 during the relative movement between the first and second clamps 72, 74. This second bending movement generally creates a second bending moment in the test piece 30 about the longitudinal axis L-A that is generally perpendicular to moment axis B-B, i.e., the first bending movement described above in FIG. 3A.

While FIG. 2 illustrates the first surface 60 and the first axis A1-A1 as generally perpendicular to the second surface 62 and the second axis A2-A2, the first and second surfaces 60 and 62 need only be oriented such that the loading device 20 exerts the first bending moment as described above. That is, the first and second surfaces 60 and 62 need not be exactly perpendicular to one another, but only perpendicular to the extent that that the first bending moment is created in the test piece 30 about the split line 94, while the second bending moment is created in the test piece 30 about the longitudinal axis L-A of the connecting rod.

The first bending moment and second bending moment created by the loading device 20 are similar to the bending moments that the crankshaft end 92 of the connecting rod experiences when operating within a reciprocating engine. More specifically, because the predetermined force of the loading device 20 substantially simulates the load and bending moments that a crankshaft end of a connecting rod experiences in a reciprocating engine, similar bending moments created in the crankshaft end of the connecting rod may also be created.

Figure 4:
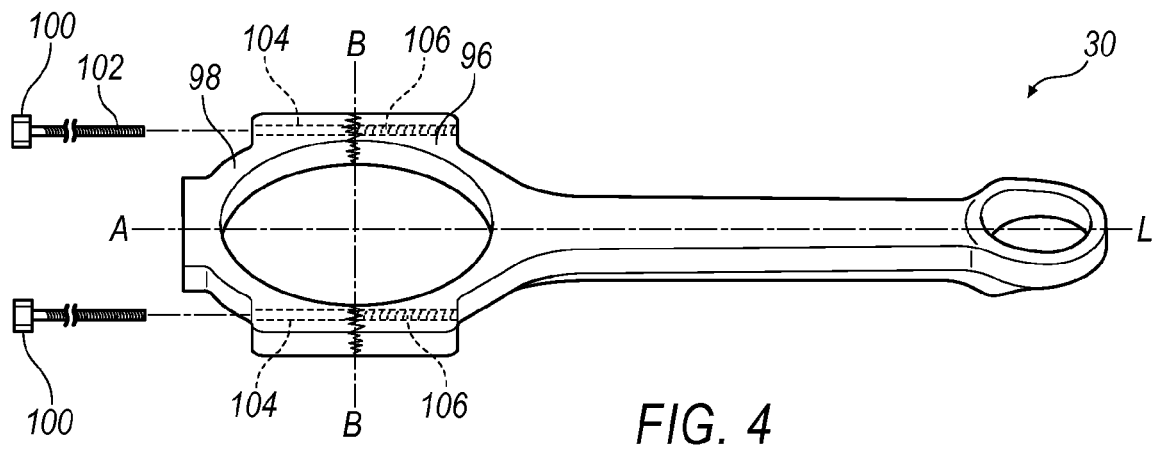
FIG. 4 is a partially exploded view of an exemplary test piece.

FIG. 4 is an exploded view of the test piece 30, which is illustrated as a connecting rod, and includes the fasteners 100 that connect the first portion 96 to the cap 98. The fasteners 100 may include threads 102, and the connecting rod may include receiving apertures 104, where the fasteners 100 are received by the receiving apertures 104. Specifically, the fasteners 100 may extend through an unthreaded portion of the apertures 104 in the cap 98 so that the threads 102 of the fasteners 100 engage complementary threads 106 inside of the apertures 104 within the first portion 96.

During operation of the loading device 20, the first and second members 34 and 36 and the first and second pairs of clamps 72 and 74 create the first and second bending moments on the test piece 30. The first and/or second bending moments generally create relative motion between the fasteners 100 and the threads 106 of the apertures 104 when the connecting rod is assembled. The relative movement between the fasteners 100 and the threads 106 tends to loosen the fasteners 100 out of the apertures 104 over a predetermined period of time, similar to the loosening that the fasteners 100 may encounter when the connecting rod operates within a reciprocating engine. The fasteners 100 may be loosened from the apertures 104 over a predetermined period of time as the loading device 20 is operated. Therefore, the loading device 20 may be used in place of a reciprocating engine during testing the connecting rod. In one exemplary illustration, the predetermined amount of time may be in the range of about 150 to about 400 hours for an engine test, however, other time periods may be used as well. By comparison, in one exemplary illustration the loading device 20 can loosen fasteners 100 after only four to five hours of operation, and in some cases within several minutes. The predetermined period of time depends on various factors, such as the fastener 100 pre-load, thread geometry and coating. The predetermined period of time also depends on the frequency and load that the loading device 20 exerts on the test piece 30.

One advantage of using the loading device 20 is that the loading device is typically more economical to use during testing of the connecting rod than a reciprocating engine. The decreased time intervals associated with creating the loosening phenomenon in a fastener 100 of a connecting rod have been noted above. Moreover, engine assemblies may create significantly different test environments for connecting rods and may therefore be very difficult to replicate even when engine designs are identical. Accordingly, the loading device 20 ensures more repeatable results as a result of the more simplified construction as compared with a reciprocating engine. Additionally, operating a reciprocating engine for several hundred hours usually requires a substantial amount of fuel to power the engine. Operating a reciprocating engine for several hundred hours may also be costly because many engine components or even the entire engine may have to be replaced.

Figure 5:
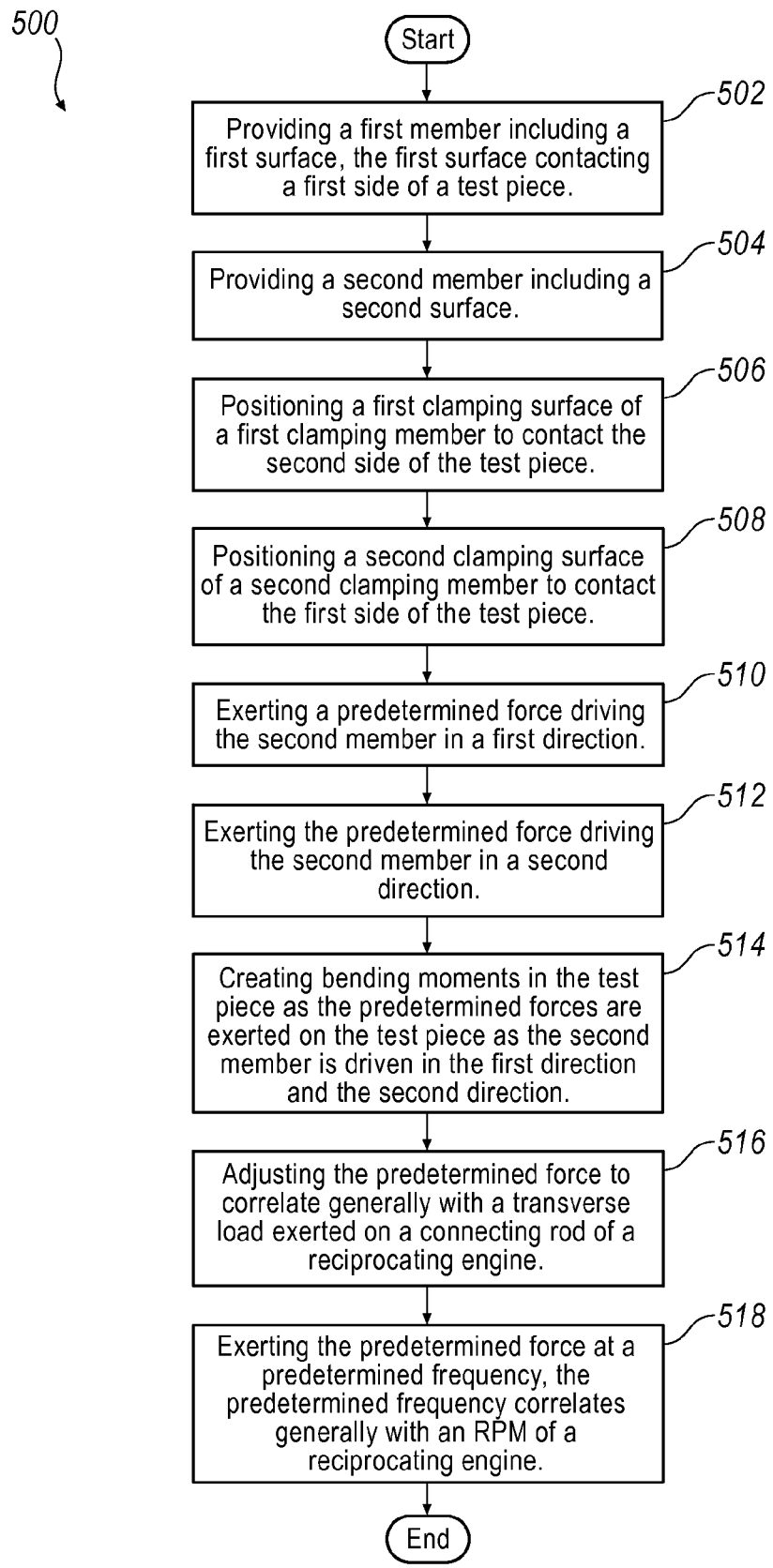
FIG. 5 is a process flow diagram of an exemplary process for exerting a force on the test piece by the loading device.

With specific reference to FIG. 5, a process 500 for creating bending moments on a crankshaft end of a connecting to simulate the load experienced on a connecting rod during operation of a reciprocating engine is described. Process 500 generally begins at steps 502. In step 502, a first member 34 is provided, where the first member 34 includes a first surface 60 that contacts a first side 28 of a test piece 30. In the illustrations of FIGS. 1-4, the test piece 30 is a connecting rod including the first side 28 and a second side 32 that generally oppose one another. Process 500 may then continue to step 504.

In step 504, a second member 36 is provided, where the second member includes a second surface 62 that may be positioned generally perpendicular to the first surface 60 as described above. The second surface contacts the second side 32 of the test piece 30 in the assembled loading device 20. Referring to FIG. 2, the first and second surfaces 60 and 62 may be generally longitudinally oriented surfaces with a width W sized for creating an edge load on the test piece 30. In one exemplary illustration, the first and second surfaces 60 and 62 may include a width of between about 2 mm and about 3 mm, measuring the width in a direction generally normal to a longitudinally extending axis of the surfaces 60, 62, e.g., axis A1-A1 and axis A2-A2, respectively. Process 500 may then continue to step 506.

In step 506, a first clamping member 72 including a first clamping surface 82 is positioned to contact the second side 32 of the test piece 30. As discussed above, the first clamping member 72 is secured to the first member 34. First fasteners 78 may be connected to the first member 34 by a threaded engagement, where the first fasteners 78 engage within first apertures 88 of the first member 34 and with first apertures 89 of the first clamping member 72 (FIGS. 1 and 2). Process 500 may then continue to step 508.

In step 508, a second clamping member 74 including a second clamp surface 84 is positioned to contact the first side 28 of the test piece 30. The second clamp surface 84 may be generally perpendicular to the first clamp surface 82, as described above. Turning to FIG. 1, when assembled to the loading device 20, the first clamp surface 82 contacts the second side 32 of the test piece 30 and the second clamp surface 84 contacts the first side 28 of the test piece 30. The second clamp surface 84 may be generally aligned with the second surface 62 of the second member 36, and the second member 36 may be fixedly connected to the second clamping members 74 when the loading device 20 is assembled. The first clamping surface 82 contacts the second side 32 of the test piece 30 and may be positioned generally perpendicular to the first clamping surface 60. The first and second clamping surfaces 82 and 84 may be generally longitudinally oriented surface with a width W' sized for creating an edge load on the test piece 30. Similar to the first and second surfaces 60 and 62, the width W' may be between about 2 mm and about 3 mm. Process 500 may then continue to step 510.

In step 510, a predetermined force drives the second member 36 in a first direction 50 away from the first member 34. Referring generally to FIG. 1, an actuator 38 may be used to communicate the predetermined force to the second member 36. As discussed above, as the second member 36 is driven in the first direction 50, the second clamp surface 84 exerts the predetermined force on the test piece 30, where the second clamp surfaces 84 may be generally aligned with the second surface 62 located on the opposing side of the test piece 30 (FIG. 3A). Process 500 may then continue to step 512.

In step 512, the predetermined force drives the second member 36 in a second direction 52 towards the first member 34. As discussed above, as the second member 36 exerts the predetermined force in the second direction 52 towards the first member 34 (illustrated in FIG. 1), the first member 34 remains generally stationary, thereby constraining the test piece 30 and creating the first and/or second bending moments in the test piece 30. Process 500 may then continue to step 514.

In step 514, bending movements in the test piece 30 are created as the predetermined forces are exerted in the first and second directions 50 and 52, thereby creating a first bending moment and a second bending moment. Specifically, as discussed above, when the second member 36 is driven in the first direction 50 (FIG. 1), the second clamp surface 84 exerts the predetermined force on the test piece 30, where the second clamp surfaces 84 may be generally aligned with the second surface 62 located on the opposing side of the test piece 30 (FIG. 3A), and positioned generally perpendicular to the split line 94. The first clamp surface 82 may be generally stationary with respect to the second clamp surface 84 as the second member 36 (FIG. 3A) is driven in the first direction 50 (FIG. 1). Therefore, relative movement between the first and second pairs of clamps 72 and 74 creates the first and second bending moments in the crankshaft end 92 of the connecting rod described above.

As the second member 36 exerts the predetermined force in the second direction 50 towards the first member 34 (illustrated in FIG. 1), the first member 34 remains relatively stationary while the second member 36 exerts the predetermined force upon the test piece 30. The relative movement between the first and second members 34 and 36 creates the first bending movement in the crankshaft end 92 of the connecting rod. Referring generally to FIG. 3B, the first bending moment is created in the test piece 30 about the split line 94, e.g., about moment axis B-B describe above. For example, as described above the movement of the second member 36 relative to the first member 34 may result in maximum displacement of the test piece 30 along longitudinal axis L-A of the test piece 30, and minimum displacement of the test piece 30 at the fracture split line 94 as the second member 36 exerts force on the test piece 30. Process 500 may then continue to step 516.

In step 516, the predetermined force is adjustable to correlate generally with a transverse load exerted on a connecting rod of a reciprocating engine. More specifically, as discussed above, the predetermined force substantially simulates approximately the same load that a connecting rod would experience while operating in a reciprocating engine, where the transverse load is typically caused by crank throw bending and crank throw to cylinder misalignment that occurs in some reciprocating engines. This is because reciprocating engines usually have some degree of bending in the crank throw as well as some degree of crank throw to cylinder misalignment. In one exemplary illustration of the loading device 20, the predetermined force is between about 2 kN and about 30 kN. Process 500 may then continue to step 518.

In step 518, the predetermined frequency correlates generally with an RPM of a reciprocating engine. For example, as discussed above, the predetermined frequency substantially simulates about the same frequency that a connecting rod would experience while operating in a reciprocating engine. The predetermined force may be adjusted independently of the predetermined frequency value, however, the predetermined force may also be adjusted in relation to the predetermined frequency value as well. In one exemplary illustration of the loading device 20, the predetermined frequency value is between about 10 Hz and about 100 Hz. Process 500 may then terminate.

Although process 500 describes the loading device 20 utilized to simulate the test piece 30 being operated within a reciprocating engine, the loading device 20 may have other uses as well. In one alternative illustration of the loading device 20, the loading device 20 may be utilized to create a connecting rod with a split-type crankshaft end, such as the connecting rod 30 with the split line 94 illustrated in FIGS. 3A, 3B, and 4. That is, referring generally to FIGS. 3A and 3B, the loading device 20 may direct a predetermined breaking force having a predetermined frequency to the connecting rod 30 such that the connecting rod 30 cracks along axis A-A, cracking apart the cap 98 from the first portion 96 of the connecting rod and creating the split line 94. For example, in one exemplary illustration, a predetermined load is applied at a frequency generally corresponding to a natural frequency of a connecting rod, thereby initiating a split fracture in the connecting rod.

More specifically, turning to FIG. 1, a test piece 30 that is a connecting rod without a split line 94 may be placed within the loading device 20. The loading device 20 may then fracture the connecting rod at the crankshaft end 92. In this illustration the connecting rod begins as a single unitary piece. The loading device 20 may then exert the predetermined breaking force in the second direction 52, where the predetermined breaking force is a value sufficient to fracture the test piece 30 into two pieces at the crankshaft end. The test piece 30 may then be removed from the loading device 20.

The present disclosure has been particularly shown and described with reference to the foregoing illustrations, which are merely illustrative of the best modes for carrying out the disclosure. It should be understood by those skilled in the art that various alternatives to the illustrations of the disclosure described herein may be employed in practicing the disclosure without departing from the spirit and scope of the disclosure as defined in the following claims. It is intended that the following claims define the scope of the disclosure and that the method and apparatus within the scope of these claims and their equivalents be covered thereby. This description of the disclosure should be understood to include all novel and non-obvious combinations of elements described herein, and claims may be presented in this or a later application to any novel and non-obvious combination of these elements. Moreover, the foregoing illustrations are illustrative, and no single feature or element is essential to all possible combinations that may be claimed in this or a later application.

What is claimed is:

1. A loading device for a test piece including a first side and a second side, the first side generally opposing the second side, the loading device comprising:
   a first member including a first surface, the first surface configured to contact the first side of the test piece;
   a first clamping member fixedly secured to the first member and including a first clamping surface, where the first clamping surface is configured to contact the second side of the test piece, the first clamping surface elongated in a first direction and defining a first longitudinal axis;
   a second member including a second surface configured to contact the second side of the test piece;
   a second clamping member fixedly secured to the second member and including a second clamping surface, wherein the second clamping surface is configured to contact the first side of the test piece, the second clamping surface elongated in a second direction and defining a second longitudinal axis, the second longitudinal axis positioned generally perpendicular to the first longitudinal axis; and an actuator in communication with the second member and configured to exert a predetermined force to drive the second member in a first loading direction away from the first member and a second loading direction toward the first member, the first loading direction being generally perpendicular to the first direction;

wherein the second clamping member is configured to exert the predetermined force on the test piece when the second member is driven in the first loading direction, and the second member is configured to exert the predetermined force on the test piece when the second member is driven in the second loading direction; and wherein the first clamping surface and the second clamping surface face in generally opposite directions, such that the first and second clamping surfaces apply opposing loads to the second and first sides of the test piece, respectively, when the second member is driven in the first loading direction.

2. The loading device of claim 1, wherein the first and second surfaces of the first and second members each are elongated to define third and fourth longitudinal axes, respectively, the third and fourth longitudinal axes being generally perpendicular to each other.

3. The loading device of claim 1, wherein the first clamping member and the second clamping member are positioned such that they cooperate to create a bending moment in the test piece when the predetermined force is exerted on the test piece.

4. The loading device of claim 1, wherein the actuator is configured to exert the predetermined force on the second member at a predetermined frequency value.

5. The loading device of claim 4, wherein the predetermined frequency value is adjustable and correlates generally with a rotational speed of a reciprocating engine associated with the test piece, and the predetermined force is adjustable and correlates generally with a transverse load exerted on a connecting rod of the reciprocating engine.

6. The loading device of claim 4, wherein the predetermined frequency value is between about 10 Hz and about 100 Hz.

7. The loading device of claim 4, wherein the predetermined frequency value is approximately equal to a natural frequency of the test piece.

8. The loading device of claim 4, wherein the predetermined force is between about 2 kN and about 30 kN.

9. The loading device of claim 1, wherein the test piece is a crankshaft end of a connecting rod.

10. The loading device of claim 9, wherein the crankshaft end of the connecting rod is split along an axis to create a split line, and the first longitudinal axis is aligned generally parallel with the split line.

11. The loading device of claim 1, wherein the first clamping surface includes two distinct first clamping surface portions spaced apart from each other along the first longitudinal axis, and the second clamping surface includes two distinct second clamping surface portions spaced apart from each other along the second longitudinal axis.

12. The loading device of claim 10, wherein the first clamping member and the second clamping member are positioned such that they cooperate to create a bending moment about the split line as the predetermined force is exerted on the connecting rod.

13. The loading device of claim 1, wherein the first surface of the first member and the second surface of the second member are each between about 2 mm and about 3 mm in width, the width measured generally orthogonally with respect to the first and second longitudinal axes of the first and second surfaces, respectively.

14. A loading device for a test piece including a first side and a second side, the first side generally opposing the second side, the test piece including two components secured together with a threaded fastener and defining a split between the two components, the loading device comprising:

a first member including a first surface, the first surface contacting the first side of the test piece;

a first clamping member fixedly secured to the first member and including a first clamping surface, the first clamping surface contacting the second side of the test piece, the first clamping surface elongated in a first direction and defining a first longitudinal axis;

a second member including a second surface contacting the second side of the test piece;

a second clamping member fixedly secured to the second member and including a second clamping surface, the second clamping surface contacting the first side of the test piece, the second clamping surface elongated in a second direction and defining a second longitudinal axis, the second longitudinal axis positioned generally perpendicular to the first longitudinal axis; and an actuator in communication with the second member and exerting a predetermined force on the second member in a loading direction generally perpendicular to the first direction;

wherein the first clamping surface and the second clamping surface face in generally opposite directions, such that the first and second clamping surfaces apply opposing loads to the second and first sides of the test piece, respectively, when the actuator exerts the predetermined force, such that the first clamping member and the second clamping member create a bending moment in the test piece about a moment axis aligned generally parallel to the split between the two components of the test piece.

15. The loading device of claim 14, wherein the first and second surfaces of the first and second members each are elongated to define third and fourth longitudinal axes, respectively, the third and fourth longitudinal axes being generally perpendicular to each other.

16. The loading device of claim 14, wherein the predetermined force is exerted on the second member at a predetermined frequency value, and the predetermined frequency value is adjustable and correlates generally with a rotational speed of a reciprocating engine associated with the test piece, and the predetermined force is adjustable and correlates generally with a transverse load exerted on a connecting rod of the reciprocating engine.

17. The loading device of claim 14, wherein the predetermined frequency value is between about 10 Hz and about 100 Hz.

18. The loading device of claim 14, wherein the first clamping surface includes two distinct first clamping surface portions spaced apart from each other along the first longitudinal axis, and the second clamping surface includes two distinct second clamping surface portions spaced apart from each other along the second longitudinal axis.

19. The loading device of claim 14, wherein the test piece is a crankshaft end of a connecting rod.

20. A method of loading a test piece, comprising the steps of:
- providing a first member including a first surface, the first surface contacting a first side of the test piece;
- positioning a first clamping surface of a first clamping member to contact the second side of the test piece, wherein the first clamping member is fixedly secured to the first member, the first clamping surface elongated in a first direction and defining a first longitudinal axis;
- providing a second member including a second surface, the second surface contacting a second side of the test piece that generally opposes the first side;
- positioning a second clamping surface of a second clamping member to contact the first side of the test piece, the second clamping member fixedly secured to the second member, the second clamping surface elongated in a second direction and defining a second longitudinal axis, the second longitudinal axis positioned generally perpendicular to the first longitudinal axis; and
- exerting a predetermined force driving the second member in a first loading direction, wherein the first loading direction is oriented away from the first member, the first loading direction being generally perpendicular to the first direction;
- wherein the second clamping member exerts the predetermined force on the test piece when the second member is driven in the first loading direction; and
- wherein the first clamping surface and the second clamping surface face in generally opposite directions, such that the first and second clamping surfaces apply opposing loads to the second and first sides of the test piece, respectively, when the second member is driven in the first loading direction.

21. The method of claim 20, further comprising exerting the predetermined force driving the second member in a second direction, the second direction being oriented towards the first member, wherein the second member exerts the predetermined force on the test piece when the second member is driven in the second direction.

22. The method of claim 20, further comprising creating a bending moment within the test piece as the predetermined force is exerted on the test piece in the first direction and the second direction.

23. The method of claim 20, further comprising:
- adjusting the predetermined force to correlate generally with a transverse load exerted on a connecting rod of a reciprocating engine; and
- exerting the predetermined force at a predetermined frequency, wherein the frequency correlates generally with a rotational speed of the reciprocating engine.

* * * * *